United States Patent [19]

Maurer et al.

[11] 4,097,593
[45] Jun. 27, 1978

[54] O-ALKYL-S-[1,6-DIHYDRO-6-THIOXO-PYRIDAZIN-(1)-YL METHYL]-(THIONO)-(DI)-THIOL-PHOSPHORIC (PHOSPHONIC) ACID ESTERS AND ESTER-AMIDES AND NEMATICIDAL, INSECTICIDAL AND ACARICIDAL COMPOSITIONS THEREOF

[75] Inventors: Fritz Maurer; Hans-Jochem Riebel, both of Wuppertal; Ingeborg Hammann, Cologne; Bernhard Homeyer, Leverkusen, all of Germany

[73] Assignee: Bayer Aktiengesellschaft, Leverkusen, Germany

[21] Appl. No.: 758,242

[22] Filed: Jan. 10, 1977

[30] Foreign Application Priority Data

Jan. 28, 1976 Germany .................. 2603052

[51] Int. Cl.² .......................... C07F 9/65; A01N 9/36
[52] U.S. Cl. .................................. 424/200; 544/232; 544/237; 544/240; 544/241; 544/239
[58] Field of Search .................. 424/200; 260/250 AP

[56] References Cited

U.S. PATENT DOCUMENTS

| 2,938,902 | 5/1960 | Du Breuil .................. 260/250 AP |
| 3,773,766 | 11/1973 | Schmidt et al. ............ 260/250 AP |
| 4,010,157 | 3/1977 | Hofer et al. ................ 260/250 AP |

FOREIGN PATENT DOCUMENTS 1,232,564  5/1971  United Kingdom .......... 260/250 AP

*Primary Examiner*—Donald G. Daus
*Assistant Examiner*—Mark L. Berch
*Attorney, Agent, or Firm*—Burgess, Dinklage & Sprung

[57] ABSTRACT

O-Alkyl-S-[1,6-dihydro-6-thioxo-pyridazin-(1)-yl methyl]-(thiono)-(di)-thiol-phosphoric (phosphonic) acid esters and ester-amides of the formula

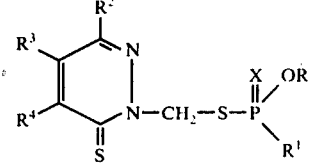

in which
R is alkyl with 1 to 6 carbon atoms,
$R^1$ is alkyl, alkoxy, alkylmercapto or alkylamino with a maximum of 6 carbon atoms per alkyl chain,
$R^2$ is halogen, alkoxy with 1 to 5 carbon atoms or alkyl with 1 to 5 carbon atoms,
$R^3$ and $R^4$ each is hydrogen or conjointly form a fused benzene ring, and
X is oxygen or sulfur atom
which possess nematicidal and arthropodicidal, e.g. insecticidal and acaricidal properties.

9 Claims, No Drawings

O-ALKYL-S-[1,6-DIHYDRO-6-THIOXO-PYRIDAZIN-(1)-YL METHYL]-(THIONO)-(DI)-THIOL-PHOSPHORIC (PHOSPHONIC) ACID ESTERS AND ESTER-AMIDES AND NEMATICIDAL, INSECTICIDAL AND ACARICIDAL COMPOSITIONS THEREOF

The present invention relates to and has for its objects the provision of particular new O-alkyl-S-[1,6-dihydro-6-thioxopyridazin-(1)-yl methyl]-(thiono)-(di)-thiol-phosphoric (phosphonic) acid esters and ester-amides which possess nematicidal and arthropodicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known from French Pat. Specification 1,231,293 and Du Breuil, J. Org. Chem. Vol. 26, No. 9 (1961), pages 3,382-3,386 that certain S-[1,6-dihydro-6-oxopyridazin-(1)-ylmethyl]-(thiono)-thiol-phosphoric acid esters, for example O,O-diethyl-S-[1,6-dihydro-6-oxo-3-methoxy- (Compound A) and -3-diethoxythionophosphoryloxy-pyridazin-(1)-ylmethyl]-thiono-thiol-phosphoric acid ester (Compound B), as well as O,O-diethyl-S-[1,2-dihydro-1-oxo-4-chlorophthalazin-(2)-ylmethyl]-thiono-thiol(Compound C) and O,O-dimethyl-O-[1,6-dihydro-6-oxo-pyridazin-(3)-yl]-thiono-phosphoric acid ester (Compound D), posses insecticidal, acaricidal and nematicidal properties.

The present invention now provides as new compounds, the S-[1,6-dihydro-6-thioxo-pyridazin-(1)-ylmethyl]-(thiono)-(di)thiol-phosphoric(phosphonic) acid ester derivatives and esteramide derivatives of the general formula

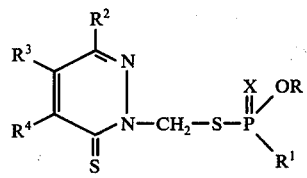

in which
R is alkyl with 1 to 6 carbon atoms,
$R^1$ is alkyl, alkoxy, alkylmercapto or alkylamino with a maximum of 6 carbon atoms per alkyl chain,
$R^2$ is halogen, or alkoxy or alkyl each with 1 to 5 carbon atoms,
$R^3$ and $R^4$ each is hydrogen or conjointly form a fused benzene ring, and
X is an oxygen or sulfur atom.

The compounds of the formula (I) are distinguished by an excellent insecticidal, acaricidal and nematicidal activity.

Preferably, R denotes a straight-chain or branched alkyl radical with 1 to 4 carbon atoms, $R^1$ denotes a straight-chain or branched alkyl, alkoxy, alkylmercapto or monoalkylamino group with 1 to 4 carbon atoms, $R^2$ denotes chlorine, methyl, ethyl, methoxy or ethoxy, and X represents sulfur.

Surprisingly, the S-[1,6-dihydro-6-thioxo-pyridazin-(1)-ylmethyl]-(thiono)-(di)-thiol-phosphoric(phosphonic) acid ester derivatives and ester-amide derivatives according to the invention possess a substantially better insecticidal, acaricidal and nematicidal action than previously known compounds of analogous structure and of the same type of action. The compounds according to the invention thus represent a genuine enrichment of the art.

The present invention also provides a process for the preparation of an S-[1,6-dihydro-6-thioxo-pyridazin-(1)-ylmethyl]-(thiono)-(di)-thiol-phosphoric(phosphonic) acid ester derivative or ester-amide derivative of the formula (I), in which (a) a 1,6-dihydro-1-halogenomethyl-6-thioxo-pyridazine of the general formula

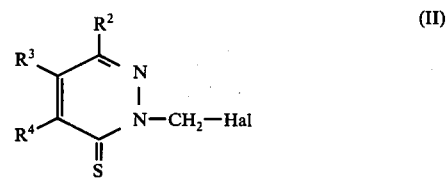

is reacted with a salt of a (thiono)(di)thiol-phosphoric (phosphonic) acid ester or ester-amide, of the general formula

or (b) a phosphorylated 1,6-dihydro-6-oxo-pyridazine derivative of the general formula

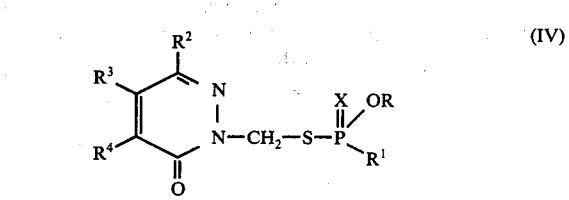

is reacted with phosphorus pentasulfide, if appropriate in the presence of an acid-binding agent; in the formulas (II) to (IV), R to $R^4$ and X have the abovementioned meanings,
Hal denotes a halogen atom, preferably a chlorine atom, and
M represents one equivalent of an alkali metal, alkaline earth metal or ammonium, preferably sodium or potassium.

If, for example, 1,6-dihydro-1-chloromethyl-3-chloro-6-thioxo-pyridazine and the potassium salt of O-ethylmethanethionothiol-phosphonic acid ester or O,O-diethyl-S-[1,6-dihydro-3-chloro-6-oxo-pyridazin-(1)-ylmethyl]-thionothiolphosphoric acid ester and phosphorus pentasulfide are used as starting materials, the two variants of the process can be represented by the following equations:

(a)

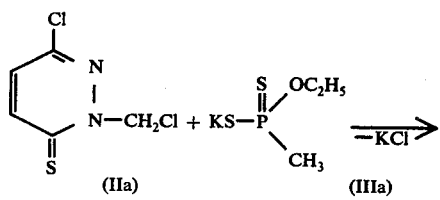

(IIa)     (IIIa)

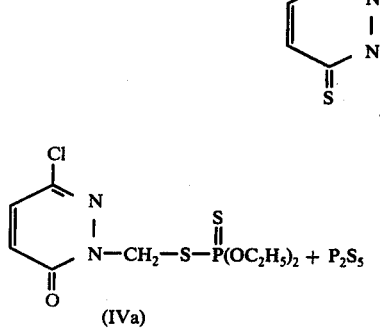

(27)

(b)

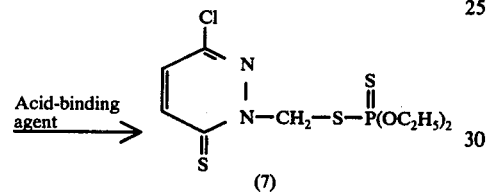

(IVa)

$$\xrightarrow{\text{Acid-binding agent}}$$

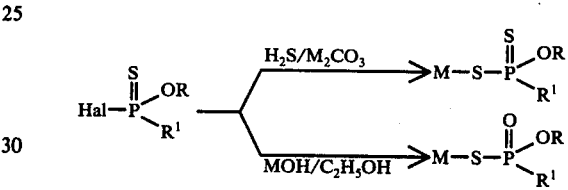

(7)

1-Halogenomethyl-6-thioxo-pyridazines of the formula (II), to be used as starting materials, are known and can be prepared in accordance with processes which are known in principle, by reacting the pyridazinones with aqueous formaldehyde solution at elevated temperatures, reacting the resulting hydroxymethyl compounds, again at elevated temperature and, if appropriate, in a solvent or diluent, with thionyl chloride, and then reacting the product with phosphorus pentasulfide, in accordance with the following reaction scheme:

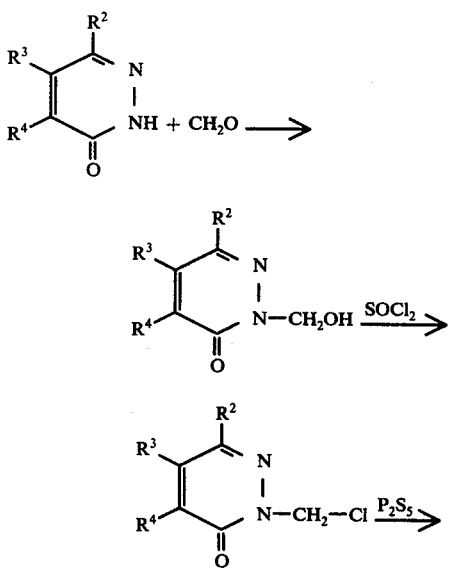

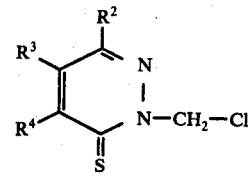

in which
R² to R⁴ have the abovementioned meanings.

The following may be mentioned as individual examples of the above compounds: 3-chloro-, 3-methoxy-, 3-ethoxy-, 3-methyl- and 3-ethyl-1,6-dihydro-6-thioxo-1-chloromethylpyridazine, and also 4-chloro-1,2-dihydro-1-thioxo-2-chloromethyl-phthalazine.

The salts of the (thiono)(di)thiolphosphoric(phosphonic) acid esters and ester-amides (III), also to be used as starting materials, are known and can be prepared in accordance with customary methods, by treating the corresponding ester halides or ester-amide halides with hydrogen sulfide in the presence of carbonates or of an alcoholic alkali solution:

$$\text{Hal}-\overset{S}{\underset{R^1}{\overset{\|}{P}}}\!\!-\!\!OR \xrightarrow[\text{MOH/C}_2\text{H}_5\text{OH}]{\text{H}_2\text{S/M}_2\text{CO}_3} \begin{array}{c} M-S-\overset{S}{\underset{R^1}{\overset{\|}{P}}}\!\!-\!\!OR \\ \\ M-S-\overset{O}{\underset{R^1}{\overset{\|}{P}}}\!\!-\!\!OR \end{array}$$

In the above equation,
Hal, R, R¹ and M have the meanings given earlier.

As individual examples of the above compounds there may be mentioned the sodium salts and potassium salts of O,O-dimethyl-, O,O-diethyl-, O,O-di-n-propyl-, O,O-di-isopropyl-, O,O-di-n-butyl-, O,O-di-iso-butyl-, O,O-di-sec.-butyl, O-methyl-O-ethyl-, O-ethyl-O-n-propyl-, O-ethyl-O-iso-propyl-, O-ethyl-O-sec.-butyl, O-ethyl-O-n-butyl-, O-ethyl-O-iso-butyl-, O-ethyl-O-tert.-butyl,O-n-propyl-O-n-butyl- and O-n-propyl-O-tert.-butyl-thiolphosphoric acid diester and the corresponding thiono analogues; the sodium salts and potassium salts of O,S-dimethyl-, O,S-diethyl-, O,S-di-n-propyl-, O,S-di-iso-propyl-, O,S-di-n-butyl-, O,S-di-isobutyl-, O,S-di-n-pentyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S-ethyl-dithiolphosphoric acid diester and the corresponding thiono analogues; the sodium salts and potassium salts of O-methyl-, O-ethyl-, O-n-propyl-, O-isopropyl-, O-n-butyl-, O-isobutyl-, O-sec.-butyl-, O-tert.-butyl- and O-n-pentyl-methane-, -ethane-, -n-propane-, -isopropane-, -n-butane-, -isobutane-, -tert.-butane- and -sec.-butane-thiolphosphonic acid ester and the corresponding thiono analogues; and the sodium salts and potassium salts of O-methyl-N-methyl-, O-methyl-N-ethyl-, O-methyl-N-n-propyl-, O-methyl-N-iso-propyl-, O-methyl-N-butyl-, O-ethyl-N-methyl-, O-ethyl-N-ethyl-, O-ethyl-N-n-propyl-, O-ethyl-N-iso-propyl-, O-ethyl-N-butyl-, O-n-propyl-N-methyl-, O-n-propyl-N-ethyl-, O-n-propyl-N-n-propyl-, O-n-propyl-N-iso-propyl, O-n-propyl-N-butyl-, O-isopropyl-N-methyl-, O-iso-propyl-N-ethyl-, O-iso-propyl-N-n-propyl-, O-iso-propyl-N-iso-propyl-, O-iso-propyl-N-butyl-, O-n-butyl-N-ethyl-, O-tert.-butyl-N- ethyl- and O-sec.-butyl-N-ethyl-thiolphosphoric acid ester-amide and their thiono analogues.

The phosphorylated 1,6-dihydro-6-oxo-pyridazine derivatives (IV), also required as starting materials, are known from the literature and can also be manufactured on an industrial scale per Belgian Patent Specification 813,225.

The following may be mentioned as individual examples of these compounds: O,O-dimethyl-, O,O-diethyl-, O,O-di-n-propyl-, O,O-di-iso-propyl-, O,O-di-n-butyl-, O,O-di-isobutyl-, O,O-di-sec.-butyl-, O-methyl-O-ethyl-, O-ethyl-O-n-propyl-, O-ethyl-O-isopropyl-, O-ethyl-O-sec.-butyl-, O-ethyl-O-n-butyl-, O-ethyl-O-isobutyl-, O-ethyl-O-tert.-butyl-, O-n-propyl-O-n-butyl- and O-n-propyl- O-tert.-butyl-S-[1,6-dihydro-6-oxo-pyridazin-(1)-ylmethyl]- and -S-[4-chloro-1,2-dihydro-1-oxo-phthalazin-(2)-ylmethyl]-thiolphosphoric acid ester and the corresponding pyridazine derivatives substituted in the 3-position by chlorine, methyl, ethyl, methoxy or ethoxy; O,S-dimethyl-, O,S-diethyl-, O,S-di-n-propyl, O,S-di-iso-propyl-, O,S-di-n-butyl-, O,S-di-iso-butyl-, O,S-di-n-pentyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S-ethyl-S-[1,6-dihydro-6-oxo-pyridazin-(1)-ylmethyl]- and -S-[4-chloro-1,2-dihydro-1-oxo-phthalazin-(2)-ylmethyl]-dithiolphosphoric acid ester and the corresponding pyridazine derivatives substituted in the 3-position by chlorine, methyl, ethyl, methoxy or ethoxy; O-methyl-, O-ethyl-, O-n-propyl-, O-iso-propyl-, O-n-butyl-, O-iso-butyl-, O-sec.-butyl-, O-tert.-butyl- and O-n-pentylmethane-, -ethane-, -n-propane-, -iso-propane-, -n-butane-, -iso-butane-, -tert.-butane-, and -sec.-butane-S-[1,6-dihydro-6-oxo-pyridazin-(1)-ylmethyl]- and -S-[4-chloro-1,2-dihydro-1-oxo-phthalazin-(2)-ylmethyl]-thiolphosphonic acid diester, and O-methyl-N-methyl-, O-methyl-N-ethyl-, O-methyl-N-n-propyl-, O-methyl-N-iso-propyl-, O-methyl-N-butyl-, O-ethyl-N-methyl-, O-ethyl-N-ethyl-, O-ethyl-N-n-propyl-, O-ethyl-N-iso-propyl-, O-ethyl-N-butyl-, O-n-propyl-N-methyl-, O-n-propyl-N-ethyl-, O-n-propyl-N-n-propyl-, O-n-propyl-N-isopropyl-, O-n-propyl-N-butyl-, O-iso-propyl-N-methyl-, O-isopropyl-N-ethyl-, O-iso-propyl-N-ethyl-, O-iso-propyl-N-n-propyl-, O-iso-propyl-N-iso-propyl-, O-iso-propyl-N-butyl-, O-n-butyl-N-ethyl-, O-tert.-butyl-N-ethyl- and O-sec.-butyl-N-ethyl-S-[1,6-dihydro-6-oxo-pyridazin-(1)-ylmethyl]- and -S-[4-chloro-1,2-dihydro-1-oxo-phthalazin-(2)-ylmethyl]-thiolphosphoric acid diester-amide and the pyridazine derivatives substituted in the 3-position by chlorine, methyl, ethyl, methoxy or ethoxy; and the corresponding thiono analogues of all the compounds listed.

The preparative process can optionally be carried out in the presence of suitable solvents or diluents. Virtually all inert organic solvents can be used for this purpose, especially aliphatic and aromatic, optionally chlorinated hydrocarbons, such as benzene, toluene, xylene, benzine, methylene chloride, chloroform, carbon tetrachloride or chlorobenzene; ethers, such as diethyl ether, dibutyl ether and dioxane; ketones, for example acetone, methyl ethyl ketone, methyl isopropyl ketone and methyl isobutyl ketone; nitriles, such as acetonitrile and propionitrile; and amides, such as dimethylformamide.

Preferred acid-binding agents which can be used in process variant (b) are weakly basic compounds, for example carbonates, such as sodium carbonate or potassium carbonate, or oxides, such as magnesium oxide.

The reaction temperature can be varied within a fairly wide range. In general, the reaction is carried out at between 0° and 120° C, preferably at 30° to 80° C, and, as a rule, under normal pressure.

To carry out process variant (a), a slight excess of the phosphoric acid salt (III) is used in most cases.

In general, the starting component (III) — if appropriate in one of the stated solvents — is added dropwise to the halogenomethylpyridazine compound (II) and the mixture is allowed to continue to react for one or more hours, if appropriate with warming. After it has cooled, an organic solvent, for example toluene, is added to the reaction mixture, which is then washed with water; the organic phase is separated off in the usual manner and dried, and the solvent is distilled off.

In process variant (b), a mixture of phosphorus pentasulfide and magnesium oxide is preferably added to the phosphorylated pyridazine component (IV), if appropriate in one of the stated solvents, the batch is allowed to finish reacting, for one or more hours, if appropriate with warming, and the undissolved constituents are filtered off. The filtrate is worked up in the usual manner, for example by washing, drying and distillation.

The compounds of this invention are in some cases obtained in the form of oils which cannot be distilled without decomposition, but are freed from the last volatile constituents by so-called "slight distillation", that is to say prolonged heating under reduced pressure to moderately elevated temperatures, and are purified in this way. They are characterized by the refractive index. Some of the products are, however, obtained in a crystalline form; in that case, they can be characterized by their melting point.

As already mentioned, the new S-[1,6-dihydro-6-thi-oxo-pyridazin-(1)-ylmethyl]-(thiono)-(di)-thiolphosphoric (phosphonic) acid ester derivatives and ester-amide derivatives are distinguished by an excellent insecticidal, acaricidal and nematicidal activity. They combine a low phytotoxicity with a good action against both sucking and biting insects.

For this reason, the compounds according to the invention can be employed successfully as pesticides in plant protection as well as in the hygiene field and the field of protection of stored products.

The active compounds are well tolerated by plants, have a favorable level of toxicity to warm-blooded animals, and can be used for combating arthropod pests, especially insects and arachnids, and nematodes which are encountered in agriculture, in forestry, in the protection of stored products and of materials, and in the hygiene field. They are active against normally sensitive and resistant species and against all or some stages of development. The abovementioned pests include:

from the class of the *Isopoda*, for example *Oniscus asellus*, *Armadillidium vulgare* and *Porcellio scaber;* from the class of the *Diplopoda*, for example *Blaniulus guttulatus;* from the class of the *Chilopoda*, for example *Geophilus carpophagus* and *Scutigera* spec.; from the class of the *Symphyla*, for example *Scutigerella immaculata;* from the order of the *Thysanura*, for example *Lepisma saccharina;* from the order of the *Collembola*, for example *Onychiurus armatus;* from the order of the *Orthoptera*, for example *Blatta orientalis*, *Periplaneta americana*, *Leucophaea maderae*, *Blattella germanica*, *Acheta domesticus*, *Gryllotalpa* spp., *Locusta migratoria migratorioides*, *Melanoplus differentialis* and *Schistocerca gregaria;* from the order of the *Dermaptera*, for example *Forficula auricularia;* from the order of the *Isoptera*, for example

*Reticulitermes* spp.; from the order of the *Anoplura*, for example *Phylloxera vastatrix, Pemphigus* spp., *Pediculus humanus corporis, Haematopinus* spp., and *Linognathus* spp.; from the order of the *Mallophaga*, for example *Trichodectes* spp. and *Damalinea* spp.; from the order of the *Thysanoptera*, for example *Hercinothrips femoralis* and *Thrips tabaci;* from the order of the *Heteroptera*, for example *Eurygaster* spp., *Dysdercus intermedius, Piesma quadrata, Cimex lectularius, Rhodnius prolixus* and *Triatoma* spp.; from the order of the *Homoptera*, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.; from the order of the *Lepidoptera*, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Doabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus holoieucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the *Hymenoptera*, for example *Diprion* spp., *Hoplocampa* spp., *Lasius* spp., *Monomorium pharaonis* and *Vespa* spp.; from the order of the *Diptera*, for example *Aëdes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the *Siphonaptera*, for example *Xenopsylla cheopis* and *Ceratophyllus* spp.; from the class of the *Arachnida*, for example *Scorpio maurus* and *Latrodectus mactans;* from the order of the *Acarina*, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp..

The plant-parasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp. and *Trichodorus* spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide disperible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, vary fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.) amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other nematicides or arthropodicides, e.g. insecticides and acaricides, or fungicides, bactericides, rodenticides, herbicides, fertilizers, growth regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.00001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. nematodes and arthropods, which comprises applying to at least one of correspondingly (a) such nematodes, (b) such arthropods, and (c) the corresponding habitat thereof, i.e. the locus to be protected, e.g. to a growing crop, to an area where a crop is to be grown or to a domestic animal, a correspondingly combative or toxic amount, i.e. a nematicidally or arthropodically effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

*Phaedon* larvae test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all the beetle larvae had been killed, whereas 0% meant that none of the beetle larvae had been killed.

The active compounds, the concentrations of the active compounds, the evaluation times and the results can be seen from the following table:

Table 1

| (*Phaedon* larvae test) | | |
|---|---|---|
| Active compound | Active compound concentration in % | Degree of destruction in % after 3 days |
| (A) (known) — pyridine ring with OCH$_3$, N-oxide, N—CH$_2$—S—P(=S)(OC$_2$H$_5$)$_2$ | 0.1<br>0.01<br>0.001 | 100<br>70<br>0 |

Table 1-continued
(*Phaedon* larvae test)

| Active compound | Active compound concentration in % | Degree of destruction in % after 3 days |
|---|---|---|
| (4) CH₃-substituted pyridazine with N—CH₂—S—P(=S)(OCH₃)₂ | 0.1<br>0.01<br>0.001 | 100<br>100<br>90 |
| (1) Cl-substituted pyridazine with N—CH₂—S—P(=S)(OCH₃)₂ | 0.1<br>0.01<br>0.001 | 100<br>100<br>100 |
| (9) CH₃-substituted pyridazine with N—CH₂—S—P(=S)(OC₂H₅)₂ | 0.1<br>0.01<br>0.001 | 100<br>100<br>95 |

EXAMPLE 2

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all the aphids were killed, whereas 0% meant that none of the aphids were killed.

The active compounds, the concentrations of the active compounds, the evaluation times and the results can be seen from the following table:

Table 2
(*Myzus* test)

| Active compound | Active compound concentration in % | Degree of destruction in % after 1 day |
|---|---|---|
|  (known) (D) | 0.1<br>0.01 | 45<br>0 |

Table 2-continued
(*Myzus* test)

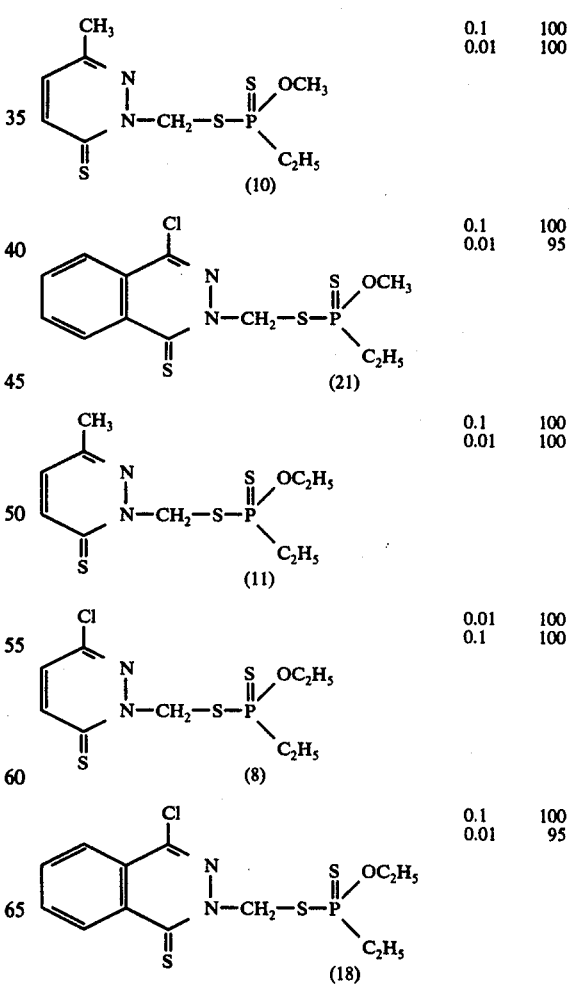

| Active compound | Active compound concentration in % | Degree of destruction in % after 1 day |
|---|---|---|
| (4) | 0.1<br>0.01 | 100<br>90 |
| (1) | 0.1<br>0.01 | 100<br>100 |
| (20) | 0.1<br>0.01 | 99<br>70 |
| (10) | 0.1<br>0.01 | 100<br>100 |
| (21) | 0.1<br>0.01 | 100<br>95 |
| (11) | 0.1<br>0.01 | 100<br>100 |
| (8) | 0.01<br>0.1 | 100<br>100 |
| (18) | 0.1<br>0.01 | 100<br>95 |

Table 2-continued
(Myzus test)

| Active compound | Active compound concentration in % | Degree of destruction in % after 1 day |
|---|---|---|
| Structure (9): 6-CH₃ pyridazine-thione with N—CH₂—S—P(=S)(OC₂H₅)₂ | 0.1<br>0.01 | 99<br>75 |
| Structure (7): 6-Cl pyridazine-thione with N—CH₂—S—P(=S)(OC₂H₅)₂ | 0.1<br>0.01 | 100<br>100 |
| Structure (19): Cl-substituted benzo-fused with N—CH₂—S—P(=S)(OC₂H₅)₂, C=S | 0.1<br>0.01 | 100<br>65 |
| Structure (6): 6-CH₃ pyridazine-thione with N—CH₂—S—P(=S)(OC₂H₅)(SC₃H₇-n) | 0.1<br>0.01 | 100<br>50 |
| Structure (12): 6-CH₃ pyridazine-thione with N—CH₂—S—P(=O)(OC₂H₅)(SC₃H₇-n) | 0.1<br>0.01 | 100<br>100 |
| Structure (15): 6-Cl pyridazine-thione with N—CH₂—S—P(=S)(OC₂H₅)(SC₃H₇-n) | 0.1<br>0.01 | 100<br>100 |
| Structure (14): 6-Cl pyridazine-thione with N—CH₂—S—P(=S)(OC₂H₅)(SC₃H₇-n) | 0.1<br>0.01 | 100<br>100 |
| Structure (5): 6-CH₃ pyridazine-thione with N—CH₂—S—P(=O)(OC₂H₅)(NH—C₃H₇-iso) | 0.1<br>0.01 | 100<br>100 |
| Structure (13): 6-CH₃ pyridazine-thione with N—CH₂—S—P(=S)(CH₃)(OC₃H₇-iso) | 0.1<br>0.01 | 100<br>100 |

EXAMPLE 3

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (Tetranychus urticae) in all stages of development were sprayed with the preparation of the active compound until dripping wet.

After the specified periods of time, the degree of destruction was determined as a percentage: 100% meant that all the spider mites were killed, whereas 0% meant that none of the spider mites were killed.

The active compounds, the concentrations of the active compounds, the evaluation times and the results can be seen from the following table:

Table 3
(Tetranychus test)

| Active compound | Active compound concentration in % | Degree of destruction in % after 2 days |
|---|---|---|
| (known) (C): Cl-substituted benzo-fused with N—CH₂—S—P(=O)(OC₂H₅)₂, C=O | 0.1 | 0 |
| Structure (4): 6-CH₃ pyridazine-thione with N—CH₂—S—P(=S)(OCH₃)₂ | 0.1 | 100 |

Table 3-continued
(Tetranychus test)

| Active compound | Active compound concentration in % | Degree of destruction in % after 2 days |
|---|---|---|
| 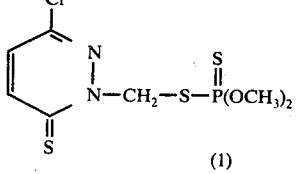 (1) | 0.1 | 100 |
| 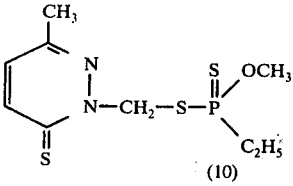 (10) | 0.1 | 100 |
| 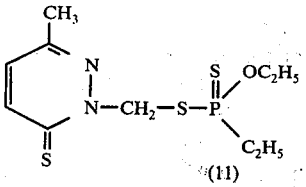 (11) | 0.1 | 100 |
| 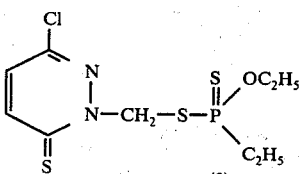 (8) | 0.1 | 99 |
| 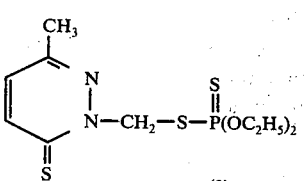 (9) | 0.1 | 98 |
| 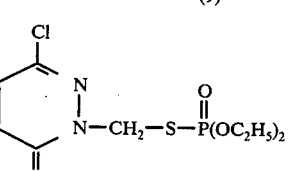 (7) | 0.1 | 98 |
| 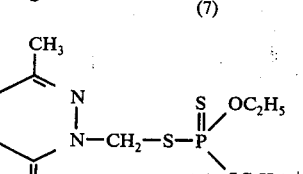 (6) | 0.1 | 98 |
| 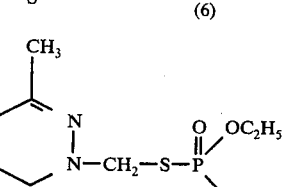 (12) | 0.1 | 99 |
| 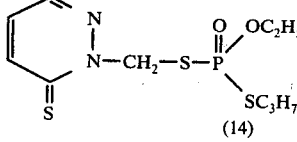 (14) | 0.1 | 99 |
| 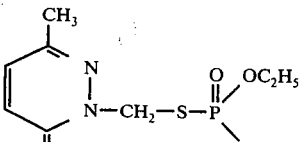 (17) | 0.1 | 100 |
| 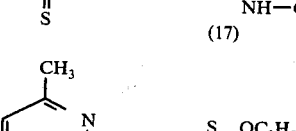 (5) | 0.1 | 100 |
| 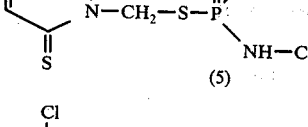 (3) | 0,1 | 98 |
| 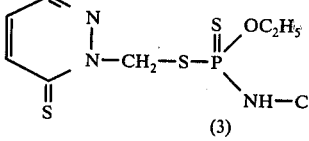 (13) | 0,1 | 100 |

EXAMPLE 4

Test insect: Phorbia antiqua grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quote hereinafter in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the table which follows:

Table 4

(*Phorbia antiqua* grubs in the soil)

| Active compound | Degree of destruction in % at an active compound concentration of 10 ppm |
|---|---|
| (known) (C) [structure] | 0 |
| (1) [structure] | 100 |
| (4) [structure] | 100 |
| (5) [structure] | 100 |
| (6) [structure] | 100 |
| (8) [structure] | 100 |
| (11) [structure] | 100 |
| (18) [structure] | 100 |
| (19) [structure] | 100 |
| (20) [structure] | 100 |
| (21) [structure] | 100 |

EXAMPLE 5

Test insect: Tenebrio molitor larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was practically immaterial, the only decisive factor being the amount by weight of active compound per unit volume of soil, which is quoted hereinafter in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all the test insects had been killed and was 0% if exactly as many test insects were still alive as in the case of the untreated control.

The active compounds, amounts used and results can be seen from the table which follows:

Table 5
*(Tenebrio molitor larvae in the soil)*

| Active compound | Degree of destruction in % at an active compound concentration of 10 ppm |
|---|---|
| (known) (C) — 2-Cl-benzene with N—CH₂—S—P(=S)(OC₂H₅)₂ structure | 0 |
| (known) (B) — (C₂H₅O)₂P(=S)—O—pyridazinone with CH₂—S—P(=S)(OC₂H₅)₂ | 0 |
| (5) — 6-CH₃-dihydropyridine-2-thione, N—CH₂—S—P(=S)(OC₂H₅)(NH—C₃H₇-iso) | 100 |
| (9) — 6-CH₃-dihydropyridine-2-thione, N—CH₂—S—P(=S)(OC₂H₅)₂ | 100 |
| (10) — 6-CH₃-dihydropyridine-2-thione, N—CH₂—S—P(=S)(OCH₃)(C₂H₅) | 100 |
| (11) — 6-CH₃-dihydropyridine-2-thione, N—CH₂—S—P(=S)(OC₂H₅)(C₂H₅) | 100 |

EXAMPLE 6

Test nematode: Meloidogyne incognita
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (= mg/l) was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compounds, the amounts applied and the results can be seen from the following table:

Table 6
*(Meloidogyne incognita)*

| Active compound | Degree of destruction in % at an active compound concentration of 10 ppm |
|---|---|
| (known) (C) — 2-Cl-benzene with N—CH₂—S—P(=S)(OC₂H₅)₂ structure | 0 |
| (known) (B) — (C₂H₅O)₂P(=S)—O—pyridazinone with CH₂—S—P(=S)(OC₂H₅)₂ | 0 |
| (2) — 6-OCH₃-dihydropyridine-2-thione, N—CH₂—S—P(=S)(OC₂H₅)(NH—C₂H₅) | 100 |
| (1) — 6-Cl-dihydropyridine-2-thione, N—CH₂—S—P(=S)(OCH₃)₂ | 100 |
| (5) — 6-CH₃-dihydropyridine-2-thione, N—CH₂—S—P(=S)(OC₂H₅)(NH—C₃H₇-iso) | 100 |

Table 6-continued
(*Meloidogyne incognita*)

| Active compound | Degree of destruction in % at an active compound concentration of 10 ppm |
|---|---|
| (8) structure with Cl, pyridazine, N-CH₂-S-P(=S)(OC₂H₅)(C₂H₅) | 100 |
| (10) structure with CH₃, pyridazine, N-CH₂-S-P(=S)(OCH₃)(C₂H₅) | 100 |
| (11) structure with CH₃, pyridazine, N-CH₂-S-P(=S)(OC₂H₅)(C₂H₅) | 100 |
| (16) structure with CH₃, pyridazine, N-CH₂-S-P(=S)(OC₃H₇-n)(NHC₃H₇-iso) | 100 |
| (17) structure with CH₃, pyridazine, N-CH₂-S-P(=S)(OC₂H₅)(NHC₂H₅) | 100 |

The process of the present invention is illustrated by the following preparative Examples.

EXAMPLE 7

(a) The preparation of the starting materials (II) was carried out, for example, as follows:

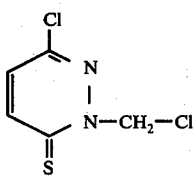

33.3 g (0.15 mole) of phosphorus pentasulfide were added to a solution of 35.8 g (0.2 mole) of 1-chloromethyl-3-chloro-1,6-dihydropyridazin-6-one (prepared as described in German Published Specification DOS 2,316,821) in 150 ml of toluene, and the mixture was stirred for 6 hours at 75°–80° C. The batch was then filtered and the solvent was stripped off under reduced pressure. The residue was recrystallized from ethanol and 19.5 g (50% of theory) of 1-chloromethyl-3-chloro-1,6-dihydro-6-thioxo-pyridazine were thus obtained in the form of yellow crystals of melting point 115° C.

The following compounds were prepared analogously:

| Structure | Yield / m.p. |
|---|---|
| CH₃-pyridazine-N-CH₂Cl (thioxo) | Yield: 54% of theory, melting point 94° C |
| Cl-phthalazine-N-CH₂Cl (thioxo) | Yield: 45% of theory, melting point 182–184° C. | b) (1) Cl-pyridazine-N-CH₂-S-P(=S)(OCH₃)₂

23.6 g (0.12 mole) of the potassium salt of O,O-dimethylthionothiolphosphoric acid diester, dissolved in 100 ml of acetonitrile, were added to a solution of 19.5 g (0.1 mole) of 1-chloromethyl-3-chloro-1,6-dihydro-6-thioxopyridazine in 100 ml of acetonitrile. The mixture was then stirred for a further 3 hours at 55° C, 300 ml of toluene were added and the mixture was washed with twice 300 ml of water. The organic phase was separated off and dried over sodium sulfate. After distilling off the solvent, 17.6 g (56% of theory) of O,O-dimethyl-S-[1,6-dihydro-3-chloro-6-thioxopyridazin-(1)-ylmethyl]-thionothiolphosphoric acid ester were obtained in the form of a yellow powder of melting point 93° C.

EXAMPLE 8

(2) OCH₃-pyridazine-N-CH₂-S-P(=S)(OC₂H₅)(NHC₂H₅)

A mixture of 8.5 g (0.0385 mole) of phosphorus pentasulfide and 8.5 g of magnesium oxide was added to a solution of 25 g (0.077 mole) of O-ethyl-N-ethyl-S-[1,6-dihydro-3-methoxy-6-oxo-pyridazin-(1)-ylmethyl]-thionothiolphosphoric acid diester-amide in 200 ml of toluene at 65° C. The mixture was allowed to react for a further 3 hours at 70°–75° C and the undissolved constituents were then filtered off. The filtrate was washed with dilute sodium hydroxide solution and water and was then dried over sodium sulphate. After adding 20 g of silica gel, the batch was filtered and the solvent was distilled off under reduced pressure. The residue was subjected to slight distillation at 80° C in a high vacuum, and 10 g (38% of theory) of O-ethyl-N-ethyl-S-[1,6-dihydro-3-methoxy-6-thioxo-pyridazin-(1)-ylmethyl]- thionothiolphosphoric acid diester-amide were thus obtained in the form of a yellow oil having a refractive index $n_D^{21}$ of 1.6555.

The following compounds of the formula

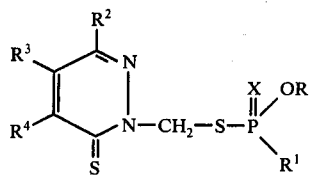

(I)

were prepared by methods analogous to those of Examples 1 and 2.

Table 7

| Compound No. | R | R$^1$ | R$^2$ | R$^3$ | R$^4$ | X | Yield (% of theory) | Physical data (Melting point °C; refractive index) |
|---|---|---|---|---|---|---|---|---|
| 3 | C$_2$H$_5$ | NH-C$_3$H$_7$-iso | Cl | H | H | S | 33 | 69 |
| 4 | CH$_3$ | OCH$_3$ | CH$_3$ | H | H | S | 47 | 83 |
| 5 | C$_2$H$_5$ | NH-C$_3$H$_7$-iso | CH$_3$ | H | H | S | 65 | 64 |
| 6 | C$_2$H$_5$ | S-C$_3$H$_7$-n | CH$_3$ | H | H | S | 61 | $n_D^{23}$: 1.6273 |
| 7 | C$_2$H$_5$ | OC$_2$H$_5$ | Cl | H | H | S | 61 | 71 |
| 8 | C$_2$H$_5$ | C$_2$H$_5$ | Cl | H | H | S | 37 | 68 |
| 9 | C$_2$H$_5$ | OC$_2$H$_5$ | CH$_3$ | H | H | S | 68 | 86 |
| 10 | CH$_3$ | C$_2$H$_5$ | CH$_3$ | H | H | S | 71 | $n_D^{20}$: 1.6438 |
| 11 | C$_2$H$_5$ | C$_2$H$_5$ | CH$_3$ | H | H | S | 78 | 60 |
| 12 | C$_2$H$_5$ | SC$_3$H$_7$-n | CH$_3$ | H | H | O | 71 | $n_D^{31}$: 1.6123 |
| 13 | C$_3$H$_7$-iso | CH$_3$ | CH$_3$ | H | H | S | 71 | 70 |
| 14 | C$_2$H$_5$ | SC$_3$H$_7$-n | Cl | H | H | O | 78 | $n_D^{32}$1.6234 |
| 15 | C$_2$H$_5$ | SC$_3$H$_7$-n | Cl | H | H | S | 68 | $n_D^{27}$: 1.6500 |
| 16 | C$_3$H$_7$-n | NH-C$_3$H$_7$-iso | CH$_3$ | H | H | S | 50 | $n_D^{25}$: 1.6326 |
| 17 | C$_2$H$_5$ | NH-C$_2$H$_5$ | CH$_3$ | H | H | S | 62 | $n_D^{25}$: 1.6402 |
| 18 | C$_2$H$_5$ | C$_2$H$_5$ | Cl | ⌬ | | S | 28 | 144 |
| 19 | C$_2$H$_5$ | OC$_2$H$_5$ | Cl | ⌬ | | S | 28 | partially crystalline |
| 20 | CH$_3$ | OCH$_3$ | Cl | ⌬ | | S | 22 | partially crystalline |
| 21 | CH$_3$ | C$_2$H$_5$ | Cl | ⌬ | | S | 31 | 95 – 97 |
| 22 | C$_2$H$_5$ | NH-C$_3$H$_{7-iso}$ | Cl | ⌬ | | S | 18 | 105 – 109 |

Other compounds which can be similarly prepared include:

Table 8

| Compound No. | R | R$^1$ | R$^2$ | R$^3$ | R$^4$ | X |
|---|---|---|---|---|---|---|
| 23 | C$_4$H$_9$ | C$_4$H$_9$ | C$_2$H$_5$ | H | H | S |
| 24 | C$_2$H$_5$ | OC$_4$H$_9$ | OC$_2$H$_5$ | H | H | S |
| 25 | C$_2$H$_5$ | SCH$_3$ | Br | H | H | S |
| 26 | C$_2$H$_5$ | NH—C$_4$H$_9$-sec. | OC$_3$H$_7$-iso | H | H | S |

It will be appreciated that the instant specification and examples are set forth by way of illustration and not limitation, and that various modifications and changes may be made without departing from the spirit and scope of the present invention.

What we claim is:

1. An O-alkyl-S-[1,6-dihydro-6-thioxo-pyridazin-(1)-ylmethyl]-(thiono)-(di)-thiol-phosphoric(phosphonic) acid ester or ester-amide of the formula

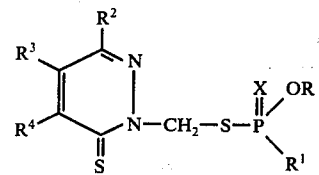

in which
R is alkyl with 1 to 6 carbon atoms,
R$^1$ is alkyl, alkoxy, alkylmercapto or alkylamino with a maximum of 6 carbon atoms per alkyl chain,
R$^2$ is halogen, alkoxy with 1 to 5 carbon atoms or alkyl with 1 to 5 carbon atoms,
R$^3$ and R$^4$ each is hydrogen or conjointly form a fused benzene ring, and
X is an oxygen or sulfur atom.

2. A compound according to claim 1, in which R is an alkyl radical with 1 to 4 carbon atoms, R$^1$ is an alkyl, alkoxy, alkylmercapto or monoalkylamino group with 1 to 4 carbon atoms, R$^2$ is chlorine, methyl, ethyl, methoxy or ethoxy, and X is sulfur.

3. The compound according to claim 1, wherein such compound is O-ethyl-N-isopropyl-S-[1,6-dihydro-3-chloro-6-thioxopyridazin-(1)-ylmethyl]-thionothiolphosphoric acid diester-amide of the formula

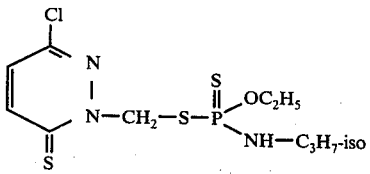

4. The compound according to claim 1, wherein such compound is O-ethyl-S-n-propyl-S-[1,6-dihydro-3- methyl-6-thioxopyridazin-(1)-ylmethyl]-thionodithiol-phosphoric acid ester of the formula

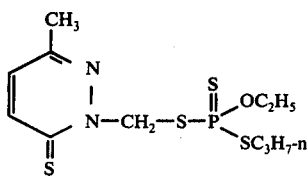

5. The compound according to claim 1, wherein such compound is O,O-diethyl-S-[1,6-dihydro-3-methyl-6-thioxopyridazin-(1)-ylmethyl]-thionothiolphosphoric acid ester of the formula

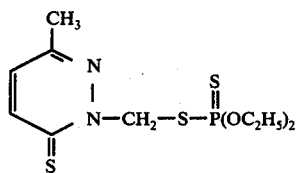

6. The compound according to claim 1, wherein such compound is O-ethyl-ethane-S-[1,6-dihydro-3-chloro-6-thioxopyridazin-(1)-ylmethyl]-thionothiolphosphonic acid ester of the formula

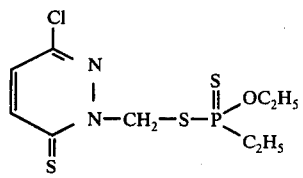

7. A nematicidal or insecticidal or acaricidal composition containing as active ingredient a nematicidally or arthropodicidally effective amount of a compound according to claim 1 in admixture with a diluent.

8. A method of combating nematodes or insects and acarids which comprises applying to the nematodes or insects and acarids or to a habitat thereof a nematicidally or insecticidally or acaricidally effective amount of a compound according to claim 1.

9. The method according to claim 8 in which said compound is O-ethyl-N-isopropyl-S-[1,6-dihydro-3-chloro-6-thioxo-pyridazin-(1)-ylmethyl]-thionothiolphosphoric acid diester-amide,
- O-ethyl-S-n-propyl-S-[1,6-dihydro-3-methyl-6-thioxo-pyridazin-(1)-ylmethyl]-thionodithiolphosphoric acid ester,
- O,O-diethyl-S-[1,6-dihydro-3-methyl-6-thioxo-pyridazin-(1)-ylmethyl]-thionothiolphosphoric acid ester, or
- O-ethyl-ethane-S-[1,6-dihydro-3-chloro-6-thioxo-pyridazin-(1)-ylmethyl]-thionothiolphosphonic acid ester.

* * * * *